United States Patent
Jung et al.

(10) Patent No.: US 11,506,654 B2
(45) Date of Patent: Nov. 22, 2022

(54) METHOD, COMPOSITION AND KIT FOR SCREENING ALK OR ROS-1 KINASE INHIBITOR

(71) Applicant: KOREA INSTITUTE OF SCIENCE AND TECHNOLOGY, Seoul (KR)

(72) Inventors: Byung Hwa Jung, Seoul (KR); Hyun Beom Lee, Seoul (KR); Naeun Yoon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 696 days.

(21) Appl. No.: 16/409,548

(22) Filed: May 10, 2019

(65) Prior Publication Data
US 2020/0132672 A1   Apr. 30, 2020

(30) Foreign Application Priority Data
Oct. 31, 2018   (KR) .................. 10-2018-0132169

(51) Int. Cl.
*G01N 33/50*       (2006.01)
*G01N 33/574*      (2006.01)

(52) U.S. Cl.
CPC ..... *G01N 33/5038* (2013.01); *G01N 33/5011* (2013.01); *G01N 33/57415* (2013.01); *G01N 33/57419* (2013.01); *G01N 33/57423* (2013.01); *G01N 33/57438* (2013.01)

(58) Field of Classification Search
CPC ................................................ G01N 33/57415
See application file for complete search history.

(56) References Cited

U.S. PATENT DOCUMENTS

2012/0208824 A1   8/2012   Rimkunas et al.

FOREIGN PATENT DOCUMENTS

| JP | 2016-166881 A | 9/2016 |
|---|---|---|
| JP | 2018-31781 A | 3/2018 |
| KR | 10-2014-0033282 A | 3/2014 |
| KR | 10-2016-0096931 A | 8/2016 |
| KR | 10-2018-0010135 A | 1/2018 |
| KR | 10-2018-0042192 A | 4/2018 |
| KR | 10-1872624 B1 | 6/2018 |

OTHER PUBLICATIONS

Blay et al., Cancer Research, 1997, 57:2603-2605.*
Rao et al., JBC, 2004, 279(24):25503-25510.*
Ayoub et al., "Crizotinib, a MET inhibitor, inhibits growth, migration, and invasion of breast cancer cells in vitro and synergizes with chemotherapeutic agents", OncoTargets and Therapy, 2017, vol. 10, pp. 4869-4883.
Crystal et al., "Variants on a Theme: A Biomarker of Crizotinib Response in ALK-Positive Non-Small Cell Lung Cancer?", Aug. 21, 2012, Clinical Cancer Research, vol. 18, pp. 4479-4482.
Lin et al., "Recent Advances in Targeting ROS1 in Lung Cancer", Journal of Thoracic Oncology, Nov. 2017, vol. 12, No. 11, pp. 1611-1625.
Pollen K. Yeung, "Metabolomics and Biomarkers for Drug Discovery", Metabolites, 2018, vol. 8, pp. 1-3.
Yasuda et al., "Preclinical rationale for use of the clinically-available multitargeted tyrosine kinase inhibitor crizotinib in ROS1 translocated lung cancer", Journal of Thoracic Oncology, Jul. 2012, vol. 7, pp. 1086-1090.
Ahmann et al., "Intracellular Adenosine Triphosphate as Measure of Human Tumor Cell Viability and Drug Modulated Growth," In Vitro Cellular & Developmental Biology (Jul. 1987), vol. 23, No. 7, pp. 474-480.
Ahn, M.-J., "Molecular Targeted Therapy in Lung Cancer," Hanyang Med. Rev. (2014), vol. 34, pp. 37-44.

* cited by examiner

*Primary Examiner* — Bin Shen
(74) *Attorney, Agent, or Firm* — Birch, Stewart, Kolasch & Birch, LLP (57) ABSTRACT

A method, a composition and a kit for screening an ALK or ROS-1 kinase inhibitor are disclosed in the present specification. In an aspect, by the method, composition and kit for screening an ALK or ROS-1 kinase inhibitor according to the present disclosure, it is possible to conduct simultaneous quantitative and qualitative analysis and faster screening of a larger number of candidate substances as compared with conventional molecular biological experimental methods and to grasp the overall level of change in a plurality of different metabolites in a cell line by candidate substances of ALK or ROS-1 kinase inhibitor and thus the screening efficiency for drugs which exert an ALK or ROS-1 kinase inhibitory effect is excellent. Consequently, the present disclosure has an advantage of being able to be used in various ways in the development of new drugs which exert an ALK or ROS-1 kinase inhibitory effect.

6 Claims, 10 Drawing Sheets

METHOD, COMPOSITION AND KIT FOR SCREENING ALK OR ROS-1 KINASE INHIBITOR

CROSS-REFERENCE TO RELATED APPLICATION

This application claims the benefit under 35 U.S.C. § 119(e) of Korean Patent Application No. 10-2018-0132169, filed on Oct. 31, 2018, which is incorporated by reference herein in its entirety.

BACKGROUND

1. Field

A method, a composition and a kit for screening an ALK or ROS-1 kinase inhibitor are disclosed in the present specification.

[Explanation on Research and Development Supported by Korean Government]

This research has been supported by the National Science and Technology Research Council of the Ministry of Science, Technology and Information Technology under the supervision of the Korea Institute of Science and Technology (Control study on biological phosphorylation signaling system based on NBIT fusion technology, Project number: 1711061857) and Korea Research Foundation of Ministry of Science and Technology Ministry of Science and Technology (Standardization of interactions of traditional natural products MC based on metabolomics, Project number: 1711058568).

2. Description of the Related Art

The crude incidence rate of all cancers (incidence rate (cancer incidence rate): the number of new cancers in a specified population during the observation period) in 2014 was 427.6 (444.9 for males and 410.3 for females) per 100,000 population, and the age-standardized incidence rate adjusted for the resident registration population of the middle of the year in 2000 (the number of population on July 1, the middle date of the year) was 289.1 (312.4 for males and 282.9 for females) per 100,000 population.

It is not easy to early detect lung cancer, which has the highest death rate among cancers, and lung cancer more often recurs and spreads to other organs than other cancers. In particular, lung cancer spreads through the lymph or blood and metastasizes mainly to other sites of the lung, bones, liver, brain, and the like. Actually, in 55% to 80% of non-small cell lung cancer patients, the cancer has already locally advanced or is found with metastasis at the time of initial diagnosis. Among these, the average survival time of the patients with brain metastasis is only 1 to 2 months without specific treatment. Accordingly, a "targeted cancer therapy" has been recently developed one after the other, and the possibility of improving the quality of life of patients and prolonging the survival time has increased. Targeted therapy exerts an anti-cancer effect by blocking the specific site of the protein pathway necessary for cancer cells to maintain their growth, differentiation, and proliferation and thus hardly affects normal cells.

In non-small cell lung cancer, a fusion oncogene through translocation, which has been found mainly in the blood cancer such as the Philadelphia chromosome, has been discovered. Representative fusion oncogene of lung cancer includes ALK and ROS-1, and as the importance of these ALK and ROS-1-rearranged non-small cell lung cancer inhibitors has come to the fore, the evaluation of drug efficacy of drug candidates in the early stage of development has become a prerequisite for successful drug development in order to develop of new drugs which inhibit non-small cell lung cancer.

Preclinical studies on targeted cancer therapies and drugs to evaluate the drug efficacy in the development of new drugs are mainly conducted through in vitro cell experiments and animal experiments. Among these, the metabolomics technique applied to the present disclosure is a study which comprehensively researches the entire small molecule metabolites (metabolome) generated during the cellular process, and it enables the observation of overall cellular conditions, metabolic conditions associated with the system, and macroscopic biochemical events in addition to the elicitation of biomarkers related to drug efficacy. Hence, the evaluation of candidate substances can be conducted in a high-throughput manner by introducing metabolomics technique into new drug development screening and screening metabolites which are changed as the drug is injected into the cells. In addition, metabolomics technique has advantages over conventional molecular biological experimental methods in that simultaneous quantitative and qualitative analysis and analysis in large quantities are possible. However, the current market for biomarkers is concentrated in the genome although it includes genomes, proteomes, and metabolic biomarkers. However, the possibility and development of new drug development screening based on omics using a proteome and a metabolome through which the function of a gene can be observed rather than a genome are coming to the fore.

Based on this, the present inventors have conducted various researches to elicit a biomarker capable of screening an ALK/ROS-1 targeted therapy through metabolomics research and to verify the functions thereof, as a result, have found out that adenosine, adenosine monophosphate (AMP), and cyclic adenosine monophosphate (cAMP) have been identified as specific biomarkers which are commonly changed by the treatment with crizotinib and ceritinib which are known as ALK/ROS-1 targeted therapies, and thus have completed the present invention.

CITATION LIST

Patent Literature

KR Patent Publication No. 10-2016-0096931
KR Patent Publication No. 10-2014-0033282
KR Patent Publication No. 10-2018-0010135

SUMMARY

In an aspect, an object of the present disclosure is to provide a method, a composition and a kit for screening an ALK or ROS-1 kinase inhibitor.

In an aspect, a method for screening an ALK or ROS-1 kinase inhibitor is provided which includes: treating a cell line with a candidate substance; measuring a level of one or more metabolites selected from a group consisting of adenosine, AMP and cAMP in the cell line treated with the candidate substance; and comparing the measured level of one or more metabolites selected from a group consisting of adenosine, AMP and cAMP with a level before being treated with the candidate substance.

In order to achieve the above object, in an aspect, the present disclosure provides a composition for screening an ALK or ROS-1 kinase inhibitor, which contains a substance detecting one or more metabolites selected from a group consisting of adenosine, AMP and cAMP as an active component.

In an aspect, the present disclosure provides a kit for screening an ALK or ROS-1 kinase inhibitor, which includes a unit for measuring a level of one or more metabolites selected from a group consisting of adenosine, AMP and cAMP.

DETAILED DESCRIPTION

Hereinafter, the present disclosure will be described in detail.

In an aspect, the present disclosure provides a method for screening an ALK or ROS-1 kinase inhibitor, which includes: treating a cell line with a candidate substance; measuring a level of one or more metabolites selected from a group consisting of adenosine, AMP and cAMP in the cell line treated with the candidate substance; and comparing the measured level of one or more metabolites selected from a group consisting of adenosine, AMP and cAMP with a level before being treated with the candidate substance. In an embodiment, the method may further include measuring a level of one or more metabolites selected from a group consisting of adenosine, AMP and cAMP in a cell line before being treated with a candidate substance.

In an embodiment, the term "screening" relates to the manipulation of selecting and/or detecting a particular metabolite(s).

In an aspect, the "ALK or ROS-1 kinase inhibitor" may include an ALK or ROS-1 kinase expression inhibitor or an ALK or ROS-1 kinase activity inhibitor, and it is a concept that may also include an ALK or ROS-1 protein tyrosine kinase inhibitor. For example, an ALK or ROS-1 kinase inhibitor may include a drug for cancer treatment, preferably it may be one or more of lung cancer treatment, a drug for breast cancer treatment, a drug for brain cancer treatment, a drug for pancreatic cancer treatment and a drug for colorectal cancer treatment, and for example, the drug for cancer treatment may be a drug for ALK or ROS-1-rearranged cancer treatment, but it is not limited thereto. The drug for lung cancer treatment generally refers to a drug for primary lung cancer of a malignant tumor originating from the lung, and for example, it may be a drug for non-small cell lung cancer treatment, a drug for small cell lung cancer treatment, or a drug for ALK or ROS-1-rearranged lung cancer treatment. For example, the non-small cell lung cancer may be lung adenocarcinoma, squamous cell carcinoma of lung, or large cell carcinoma of lung. For example, the ALK or ROS-1 rearrangement may be that the tyrosine at position 1604 from the N-terminus of the ALK protein is phosphorylated or that the tyrosine at position 2274 from the N-terminus of the ROS-1 protein is phosphorylated, but it is not limited thereto.

In an embodiment, the composition may further contains one or more cell lines selected from the group consisting of a lung carcinoma cell line, a breast carcinoma cell line, a brain cancer cell line, a pancreatic cancer cell line, and a colorectal cancer cell line as an active component, each of the cell lines may be a lung carcinoma cell line, a breast carcinoma cell line, a brain cancer cell line, a pancreatic cancer cell line and a colorectal cancer cell line in an embodiment, and in another embodiment, the cell lines may be ALK or ROS-1-overexpressing cell lines, but they are not limited thereto. In an embodiment, the "overexpression" may mean that the expression level of ALK or ROS-1 is higher than that of normal cells in each tissue by 1.1 times or more, 1.2 times or more, 1.3 times or more, 1.4 times or more, 1.5 times or more, 1.6 times or more, 1.7 times or more, 1.8 times or more, 1.9 times or more, 2.0 times or more, 2.5 times or more, 3 times or more, 3.5 times or more, 4 times or more, 4.5 times or more, 5 times or more, 10 times or more, 15 times or more, 20 times or more, 25 times or more, 30 times or more, 35 times or more, 40 times or more, 45 times or more, or 50 times or more, but it is not limited to.

For example, the lung carcinoma cell line may be a non-small cell lung carcinoma cell line or a small cell lung carcinoma cell line, or the lung carcinoma cell line may be an ROS-1 or ALK-overexpressing lung cancer cell line. More preferably, the lung carcinoma cell line may be an H3122 cell line, which is an ALK-overexpressing lung cancer cell line, or an HCC-78 cell line, which is an ROS-1 overexpressing lung cancer cell line, and most preferably, it may be an HCC-78 cell line, but it is not limited thereto. The HCC-78 cell line used in the disclosure has been deposited under an accession number of KCTC13642BP.

For example, the breast carcinoma cell line may be a carcinoma in situ of breast cell line, more preferably it may be an MCF-7 cell line, an MDA-MB-231 cell line, and an SK-BR-3 cell line, and most preferably it may be an MCF-7 cell line, but it is not limited thereto. The MCF-7 cells are cells which express ALK and ROS-1 but are not cells which overexpress these, and the technical specificity is in that the MCF-7 cells can be used for screening of an ALK or ROS-1 kinase inhibitor. The carcinoma in situ of breast cell line may be referred to as a breast cancer epithelial cell line, and the MCF-7 cell line used in the disclosure has been deposited under an accession number of KCTC13643BP.

In an embodiment, the method may further include conducting multivariate analysis of the measured level of metabolites, and the multivariate analysis is, for example, a statistical analysis in which changes in the body level of two or more metabolites specifically change in the subject cell line by a candidate substance effective in ALK or ROS-1 kinase inhibition are simultaneously analyzed.

In an embodiment, the method may further include judging a candidate substance to be suitable as an ALK or ROS-1 kinase inhibitor when the content of adenosine or cAMP in the cell line is higher than that before being treated with the candidate substance and judging a candidate substance to be unsuitable as an ALK or ROS-1 kinase inhibitor when the content of adenosine or cAMP in the cell line is lower than or equal to that before being treated with the candidate substance.

In an embodiment, the method may further include judging a candidate substance to be suitable as an ALK or ROS-1 kinase inhibitor when the content of AMP in the cell line is lower than that before being treated with the candidate substance and judging a candidate substance to be unsuitable as an ALK or ROS-1 kinase inhibitor when the content of AMP in the cell line is higher than or equal to that before being treated with the candidate substance.

In an embodiment, a candidate substance is classified as a metabolite which exhibits a significant change when the p value is 0.15 or less, 0.14 or less, 0.13 or less, 0.12 or less, 0.11 or less, 0.1 or less, 0.09 or less, 0.08 or less, 0.07 or less, 0.06 or less, 0.05 or less, 0.04 or less, 0.03 or less, 0.02 or less, or 0.01 or less after the change value in the content of a metabolite before and after being treated with the candidate substance has been subjected to a t-test, and preferably the candidate substance is classified as a metabolite which exhibits a significant change when the p value is 0.05 or less. Alternatively, in an embodiment, it may be classified that there is no significant difference when the percentage difference with respect to the change in the content of each metabolite before and after being treated with the candidate substance is ±28 or less, ±27 or less, ±26 or less, ±25 or less, ±24 or less, ±23 or less, ±22 or less, ±21 or less, ±20 or less, ±19 or less, ±18 or less, ±17 or less, ±16 or less, ±15 or less, ±14 or less, ±13 or less, ±12 or less, ±11 or less, ±10 or less, ±9 or less, ±8 or less, ±7 or less, ±6 or less, ±5 or less, ±4 or less, ±3 or less, ±2 or less, or ±1 or less, but the disclosure is not limited thereto.

In an aspect, the present disclosure provides a composition for screening an ALK or ROS-1 kinase inhibitor, which contains a substance detecting one or more metabolites selected from a group consisting of adenosine, AMP and cAMP as an active component.

In an embodiment, the "substance which detects a metabolite" includes any substance capable of detecting metabolites including adenosine, AMP, and cAMP without limitation. For example, the substance which detects a metabolite may be an antibody, an enzyme in an ELISA kit, and the like, and more specifically it may be an antibody such as anti-cAMP (LifeSpan BioSciences, Inc., #LS-C121425-50), an AMP ELISA kit (#ABIN2051817), and the like.

In an aspect, the present disclosure provides a kit for screening an ALK or ROS-1 kinase inhibitor, which includes a unit for measuring the level of one or more metabolites selected from a group consisting of adenosine, AMP and cAMP.

In an embodiment, the "level of a metabolite" is the broadest meaning including both objective values such as the concentration and mass of the metabolites contained in the sample and the relative amounts of a substance to those of other substances.

In an embodiment, the kit may further contain one or more cell lines selected from the group consisting of a lung carcinoma cell line, a breast carcinoma cell line, a brain cancer cell line, a pancreatic cancer cell line, and a colorectal cancer cell line.

In an embodiment, the metabolite level measuring unit of the kit may contain the composition for screening described above.

In an embodiment, the kit may further include a multivariate analysis system for analyzing levels of metabolites measured in the metabolite level measuring unit, and the multivariate analysis system is, for example, a statistical analysis in which changes in the body level of two or more metabolites among three or more metabolites which specifically change in the subject cell line by a candidate substance effective in ALK or ROS-1 kinase inhibition are simultaneously analyzed.

In an embodiment, the kit may further include a method for screening an ALK or ROS-1 kinase inhibitor or an instruction manual including the instructions on the metabolite to be screened. For example, the instruction manual may include pamphlets or information brochures in the form of leaflets, labels attached to the kit, and the instructions written on the surface of the package including the kit, and it may further include guidebooks which include information to be disclosed or provided through an electronic medium such as the Internet and the like.

The redundant contents are omitted in consideration of the complexity of the present specification, and terms not otherwise defined herein have the meanings commonly used in the art to which the present disclosure belongs. In addition, the term "or" in the present specification should be understood as including the term "and" unless otherwise noted.

Hereinafter, the present disclosure will be described in detail with reference to the following Examples. It should be noted, however, that the following Examples are illustrative of the present disclosure and are not intended to limit the scope of the present disclosure. Examples of the present disclosure are provided to more fully describe the present disclosure to those skilled in the art.

Example 1. Confirmation of Cell Viability of Lung Carcinoma Cell Line or Breast Carcinoma Cell Line Against ALK/ROS-1-Specific Kinase Inhibitor In order to confirm whether a lung carcinoma cell line or a breast carcinoma cell line can be used as a cell line suitable for screening of an ALK/ROS-1-specific kinase inhibitor, each of the cell lines was treated with a known ALK/ROS-1-specific kinase inhibitor and then subjected to WST-1 assay and MTT assay, respectively, to confirm a change in the cell viability.

1-1. Confirmation of Cell Growth Inhibitory Effect on Lung Carcinoma Cell Line (HCC-78) by WST-1 Assay The growth inhibition rate of HCC-78 cell line by crizotinib and ceritinib of an ALK-specific enzyme inhibitor and a ROS-1-specific enzyme inhibitor was confirmed by conducting WST-1 assay according to the method commonly used in the art. Specifically, HCC-78 lung cancer cells deposited under an accession number of KCTC13642BP on Sep. 17, 2018 were cultured in a 5% carbon dioxide cell incubator at a temperature of 37° C. using a DMEM medium containing 10% fetal bovine serum and 1% antibiotic until the number of cells in each well of a 96-well plate reached $5.2 \times 10^3$. Thereafter, when the cell growth was stabilized, the cells were treated with each of crizotinib and ceritinib as ALK and ROS-1 kinase inhibitors so as to have a percentage of 0.01% of the total medium and a concentration of 1 μM and then cultured for 24, 48, and 72 hours, respectively. At this time, DMSO (dimethyl sulfoxide) was added to a control group in an amount to be 0.01% of the total medium, 1 μM doxorubicin was added to a positive control group, and then these control group and positive control group were cultured for 24, 48, and 72 hours, respectively. In addition, the experiment was conducted using an A549 cell line instead of the HCC cell line as a negative control group. The A549 cell line is a kRAS mutant cell line and is also a cell line which is not involved in the overexpression of ALK and ROS-1.

When each of the culture times passed after drug treatment, the WST-1 reagent was added to each medium in an amount to be 10% of the medium, the cells were cultured for 1 hour, and then the absorbance of cells was measured at 470 nm by using an ELISA instrument. The resulting cell growth graph for the HCC-78 cell line is illustrated in FIG. 1 and the resulting cell growth graph for the A549 cell line of a negative control group is illustrated in FIG. 2.

Figure 1:
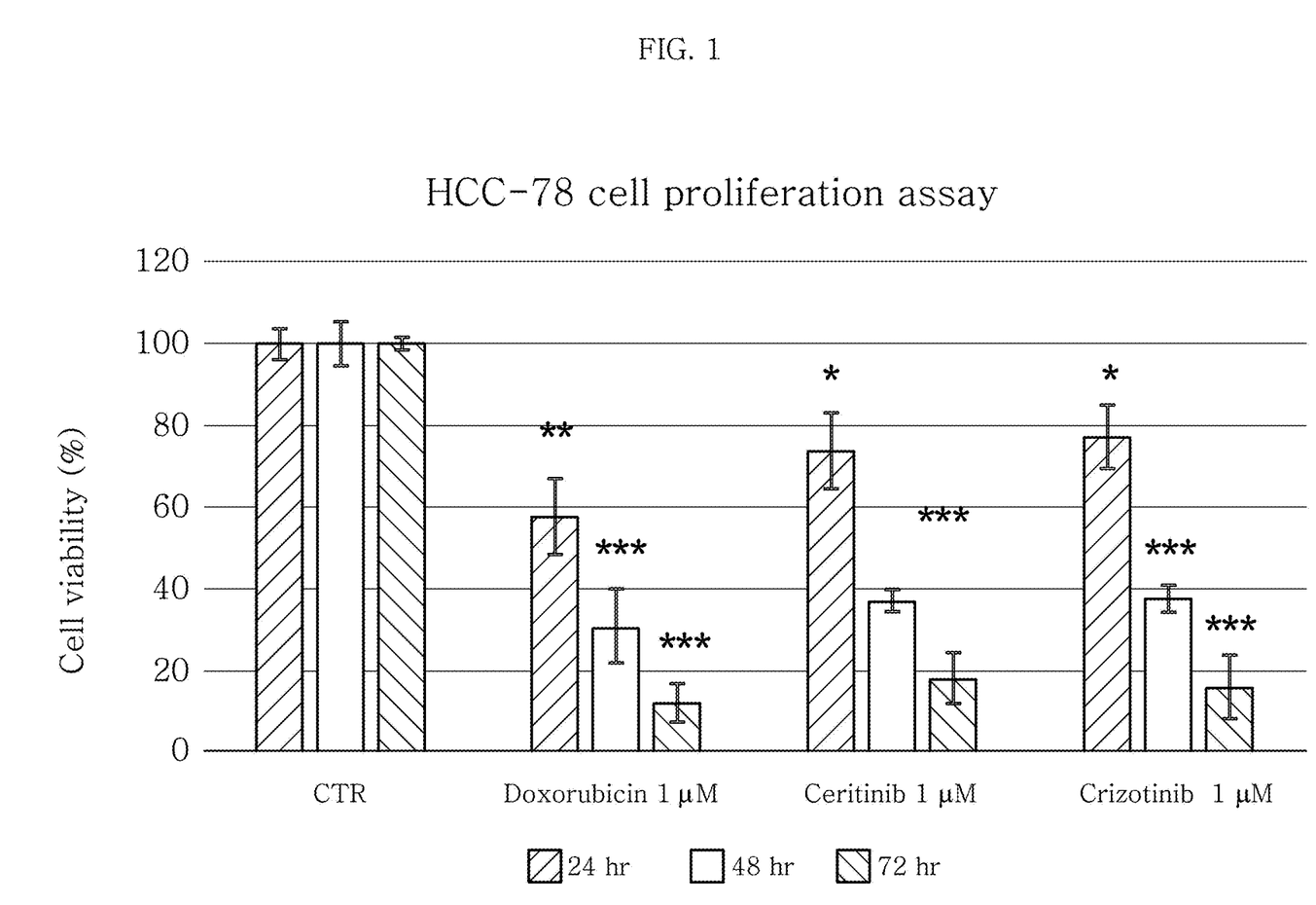
FIG. 1 is a graph illustrating the results of confirming the cell growth inhibitory effect on a lung carcinoma cell line (HCC-78) through WST-1 assay.
Figure 2:
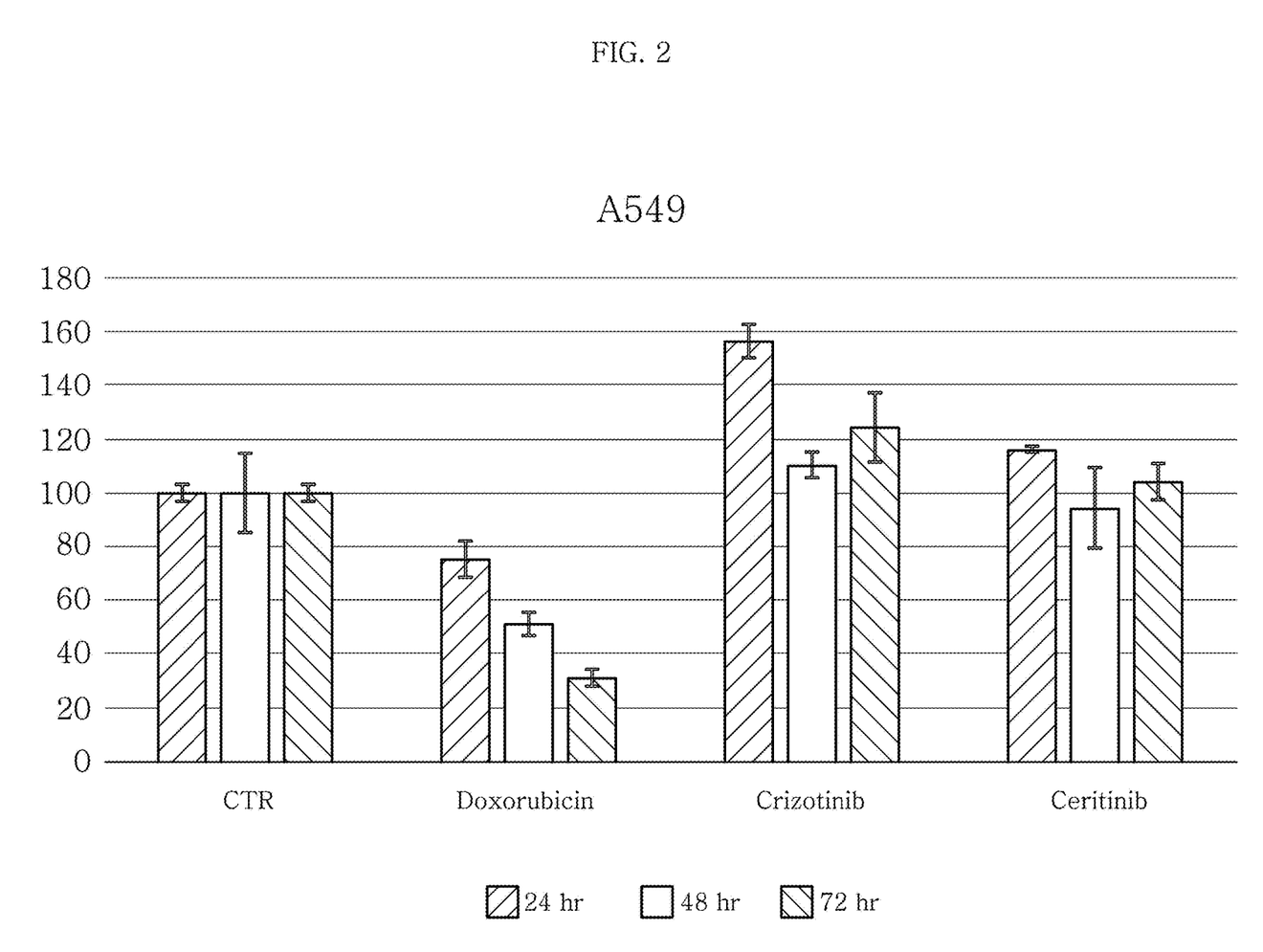
FIG. 2 is a graph illustrating the results of confirming the cell growth inhibitory effect on an A549 cell line through WST-1 assay.

As can be seen from FIGS. 1 and 2, it has been confirmed that both crizotinib and ceritinib of ALK/ROS-1-specific kinase inhibitors significantly inhibited, particularly time dependently inhibited the growth of HCC-78 cells but both crizotinib and ceritinib were not able to significantly inhibit the growth of the A549 cells of a negative control group (Student's t-test, p<0.05). Specifically, when it is assumed that the control group exhibited a growth rate of 100%, the growth rates of HCC-78 cells were 77.13% and 73.73% in the groups treated with crizotinib and ceritinib, respectively, when 24 hours had elapsed after the HCC-78 cells were treated with each of these substances, and the growth rate of HCC-78 cells was 57.65% in the group treated with doxorubicin of a positive control group. When 48 hours and 72 hours had elapsed after the HCC-78 cells were treated with each of these substances, the growth rate of HCC-78 cells was 37.63% and 16.04%, respectively, in the group treated with crizotinib and the growth rate of HCC-78 cells was 37.17% and 17.99%, respectively, in the group treated with ceritinib as well. This indicates that HCC-78 cells can be used for screening an ALK/ROS-1 kinase inhibitor.

1-2. Confirmation of Cell Viability of Breast Cancer Cell Line (MCF-7) Through MTT Assay The growth inhibition rate of MCF-7 breast cancer cells by crizotinib was confirmed by conducting MTT assay according to the method commonly used in the art. Specifically, MCF-7 breast cancer cells deposited under an accession number of KCTC13643BP on Sep. 17, 2018 were cultured in a 5% carbon dioxide cell incubator at a temperature of 37° C. using a DMEM medium containing 10% fetal bovine serum and 1% antibiotic until the number of cells in each well of a 96-well plate reached $1.3 \times 10^3$. Thereafter, when the cell growth was stabilized, each well was treated with each of crizotinib and six kinds of kinase inhibitors (dabrafenib, defactinib, lapatinib, regorafenib, gefitinib, and crizotinib) so as to have a percentage of 0.01% of the total medium and a concentration of 1 μM and then the cells were cultured for 72 hours. At this time, DMSO (dimethyl sulfoxide) was added to a control group in an amount to be 0.01% of the total medium, 1 μM paclitaxel was added to a positive control group, and then these control group and positive control group were cultured for 72 hours.

When each of the culture times passed after drug treatment, the supernatant of each medium was removed, the MTT reagent was added to the fresh medium so as to be 0.5 mg/ml, the cells were cultured for 3 hours, then the supernatant was removed again, and then the medium was reconstituted with 100 μL of DMSO. Thereafter, the absorbance of cells was measured at 590 nm by using an ELISA instrument. The resulting growth graph for the cells is illustrated in FIG. 3.

Figure 3:
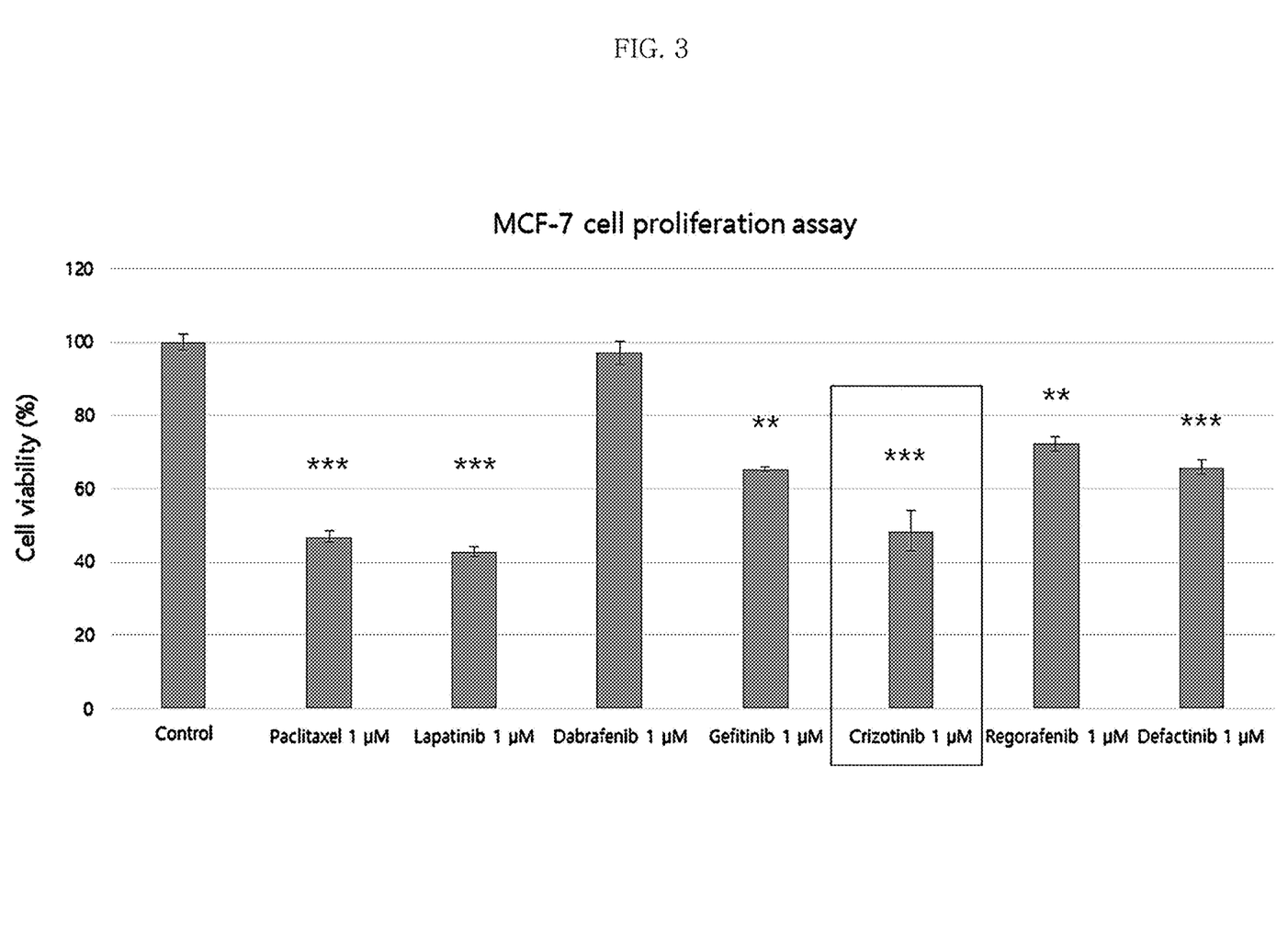
FIG. 3 is a graph illustrating the results of confirming the cell viability of a breast carcinoma cell line (MCF-7) through MTT assay.

As can be seen from FIG. 3, it has been confirmed that 5 kinds of kinase inhibitors except dabrafenib significantly inhibited the cell growth of the MCF-7 cell line (Student's t-test, p value <0.05). In addition, it has been observed that the cell growth rate was 48.45% as compared with that of the control group when the cells were treated with crizotinib. The cell growth rate was 46.86% in the group treated with paclitaxel of a positive control group, and thus the group treated with crizotinib and the positive control group have similar levels of cell growth inhibitory ability (Student's t-test, p<0.001). Consequently, it can be seen that several kinase inhibitors inhibit cell growth of MCF-7, and at the same time, the MCF-7 cell line having a significant cell growth inhibition rate by crizotinib is suitable as a cell line to be used for screening an ALK or ROS-1 kinase inhibitor.

Example 2. Treatment of Lung Carcinoma Cell Line or Breast Carcinoma Cell Line with ALK/ROS-1 Kinase Inhibitor and Isolation and Analysis of Metabolites Using Mass Spectrometer In order to elicit metabolites which are changed by being treated with an ALK or ROS-1 kinase inhibitor, namely, metabolites which can be used for screening ALK or ROS-1 kinase inhibitors, a lung carcinoma cell line or a breast carcinoma cell line, which is a cell line suitable for screening of ALK or ROS-1 kinase inhibitors was treated with known ALK or ROS-1 kinase inhibitors, and then the metabolites changed in each cell line were analyzed.

2-1. Culture of lung carcinoma (HCC-78) and breast carcinoma (MCF-7) and acquisition of cells after treatment of cells with ALK or ROS-1 kinase inhibitor.

2-1-1. Culture of HCC-78 and Treatment of HCC-78 with Crizotinib and Ceritinib as ALK or ROS-1 Kinase Inhibitor HCC-78 lung cancer cells were cultured in a 5% carbon dioxide cell incubator at a temperature of 37° C. using a RPMI medium containing 10% fetal bovine serum and 1% antibiotic. Thereafter, when the cell growth was stabilized, the cells were treated with each of crizotinib and ceritinib of ALK and ROS-1 kinase inhibitors at a concentration of 1 μM so as to have a percentage of 0.01% of the total medium and then cultured for 24 hours. At this time, as a control group, DMSO (dimethyl sulfoxide) was added to the cells in an amount to be 0.01% of the total medium, and the cells were cultured for 24 hours. Each cell was cultured in 5 cell dishes for each group so that the total number of experiments for each group was 5 (n=5).

After the culture time of 24 hours had elapsed, the medium was removed, and the cells were washed two times with PBS (phosphate buffered saline). The cells were then acquired from the culture dish using a cell scraper, put in a tube, and stored at −80° C.

2-1-2. Culture of MCF-7 and Treatment of MCF-7 with Crizotinib as ALK or ROS-1 Kinase Inhibitor MCF-7 breast cancer cells were cultured in a 5% carbon dioxide cell incubator at a temperature of 37° C. using a DMEM medium containing 10% fetal bovine serum and 1% antibiotic. Thereafter, when the cell growth was stabilized, the cells were treated with crizotinib to be used as an ALK or ROS-1 kinase inhibitor at a concentration of 1 µM so as to have a percentage of 0.01% of the total medium and then cultured for 12 hours. At this time, as a control group, DMSO was added to the cells in an amount to be 0.01% of the total medium, and the cells were cultured for 12 hours. Each cell was cultured in 5 cell dishes for each group so that the total number of experiments for each group was 5 (n=5).

After the culture time of 12 hours had elapsed, the medium was removed, and the cells were washed two times with PBS. The cells were then acquired from the culture dish using a cell scraper, put in a tube, and stored at −80° C.

2-2. Intracellular Fluid Extraction and DNA Quantification

For mass analysis, 120 µL of a 70% methanol solution containing 2 µg/mL of reserpine as an internal standard substance was added to the cells obtained in Example 2-1, and then the mixture was subjected to vortexing so as to allow the cells to mix well. Thereafter, a process in which the mixed solution was frozen using liquid nitrogen, dissolved in water at room temperature, and then sonicated for 30 seconds was repeated three times to destroy the cells. Thereafter, the resultant mixed solution was subjected to centrifugation at 14000 rpm for 10 minutes, and only the supernatant was separated from this. At this time, DNA quantitation was conducted in order to correct the cell volume of the intracellular fluid extract acquired according to the series of procedures. DNA quantitation was conducted by mixing the extract with water at a ratio of 1:3, putting 5 µL of the mixture in a cuvette, and measuring the quantity at 260 nm by using a spectrophotometer Nano-MD of SHINKO CO., LTD.

2-3. Analysis by Ultra-High-Performance Liquid Chromatography-Mass Spectrometry (UHPLC-MS)

Each sample pretreated according to Example 2-2 was subjected to analysis of metabolites in the sample by using an ultra-high-performance liquid chromatography system-mass spectrometer (Ultimate 300 UPHLC system-Orbitrap velos pro system mass spectrometer of Thermo Fisher Scientific Inc., Molecular Cognition Research Center of Korea Institute of Science and Technology).

Figure 4:
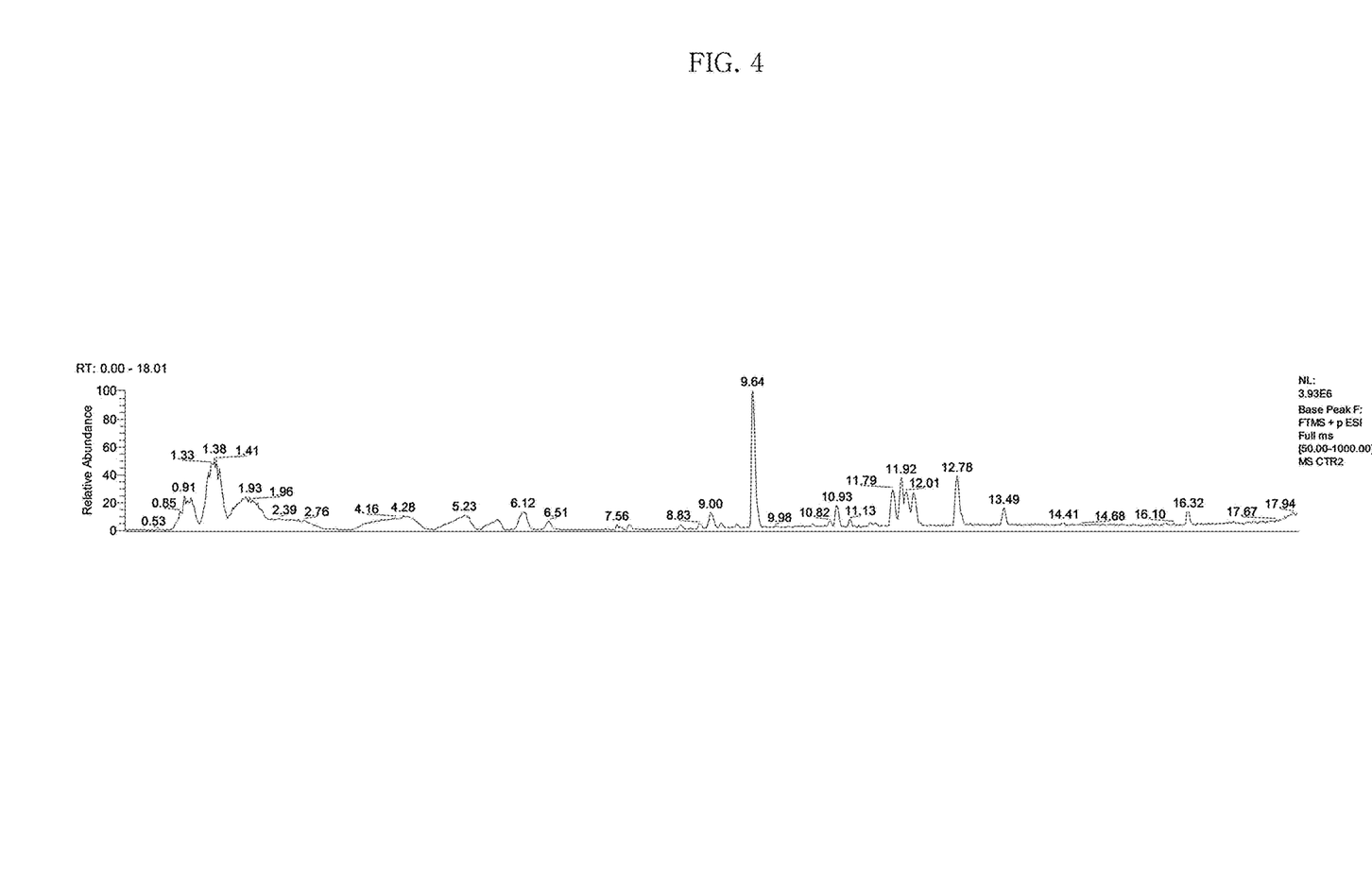
FIG. 4 is a graph illustrating the results of analyzing a change in metabolites after a lung carcinoma cell line (HCC-78) has been treated with an ALK/ROS-1 kinase activity inhibitor by ultra-high-performance liquid chromatography-mass spectrometry (UHPLC-MS)
Figure 5:
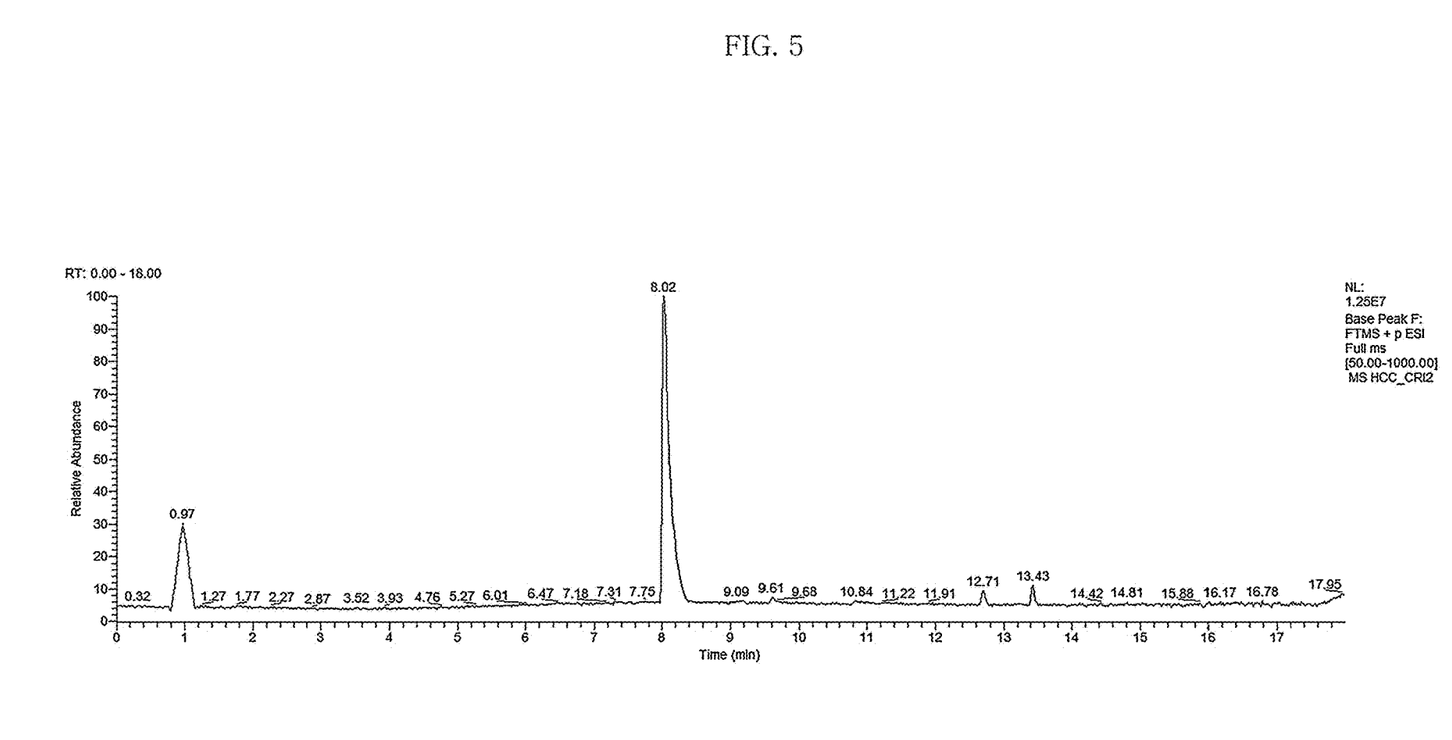
FIG. 5 is a graph illustrating the results of analyzing a change in metabolites after a breast carcinoma cell line (MCF-7) has been treated with an ALK/ROS-1 kinase activity inhibitor by ultra-high-performance liquid chromatography-mass spectrometry.

Specifically, 10 µL of the acquired sample was injected into the ultra-high-performance liquid chromatography system-mass spectrometer, and the temperature of the injector was maintained at 4° C. As the ultra-high-performance liquid chromatography conditions, water (mobile phase A) containing 0.1% formic acid and methanol (mobile phase B) containing 0.1% formic acid were used as the solutions. The column used was ACQUITY® HSS T3 (2.1×100 mm, 1.7 µm) of Waters Corporation, and the temperature of the column was maintained at 40° C. The analysis was conducted by a gradient elution method in which two mobile phases were mixed in the UPLC system at different ratios according to the analysis time and allowed to flow. At this time, as the gradient of the mobile phases for liquid chromatography, the solution A was maintained at 99% from 0 minute until second minute, the B solution was increased to 100% until 14th minute, then the B solution was maintained at 100% until 15th minute, and the condition was then set to the initial condition for 3 minutes. The flow of solution was maintained at 0.4 mL. The mass spectrometry was conducted in both of the positive mode and the negative mode. The temperature of the source of the mass spectrometer was set to 300° C., and the solvent delay time was set to 3 minutes. During the analysis, QC (quality control) samples were added to the sequence for the quality control of analysis, and it was confirmed that there was no problem with the equipment in the whole process of analysis. As the QC samples, those prepared by pooling sample extracts of both the control group and the experimental group were used. The results for the experiment on the HCC-78 cell line among the resulting chromatograms are illustrated in FIG. 4, and the results for the experiment on the MCF-7 cell line are illustrated in FIG. 5.

2-4. Chromatogram Data Analysis and Statistical Processing

Figure 6:
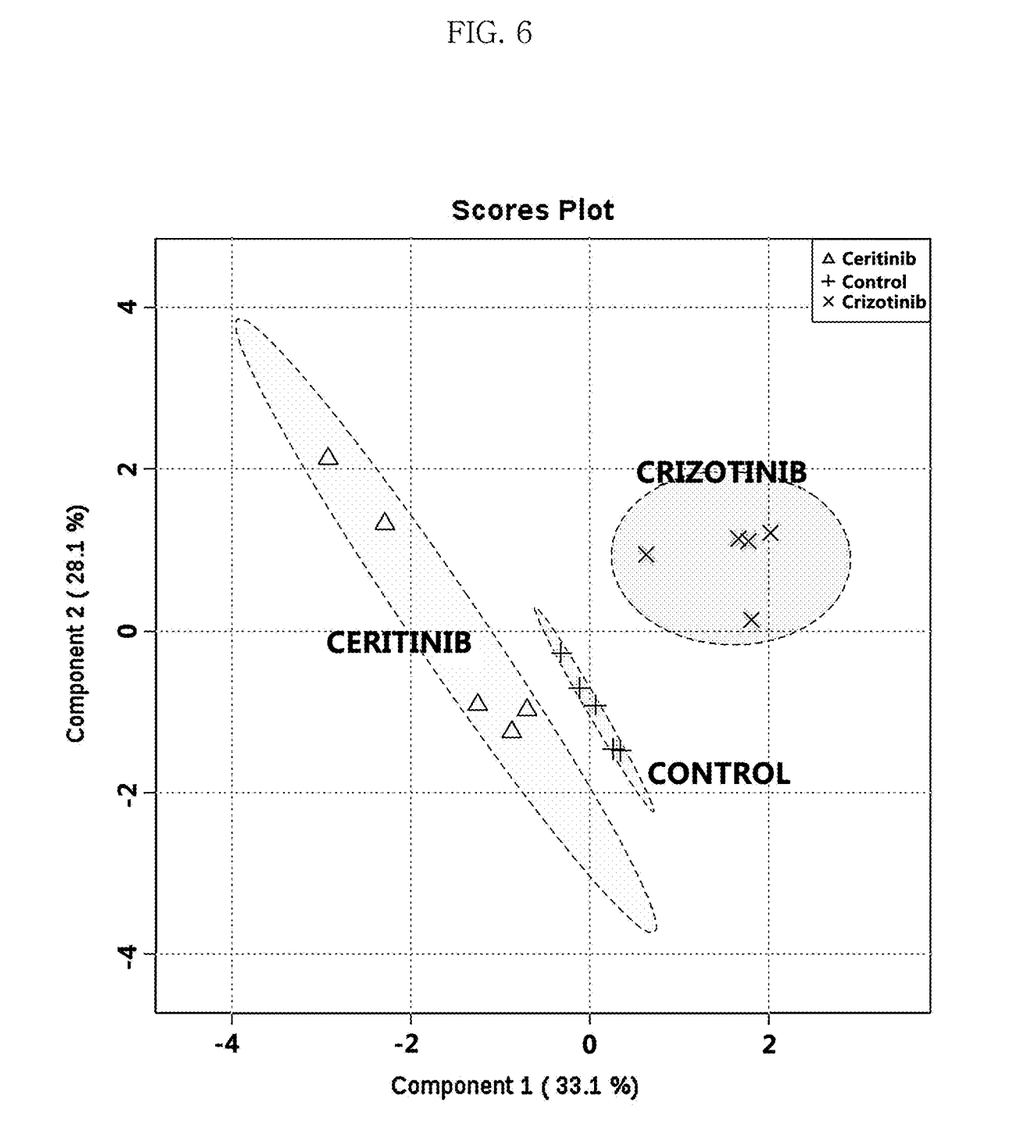
FIG. 6 is a diagram illustrating the results of the chromatogram data analysis of the result values illustrated in FIG. 4.
Figure 7:
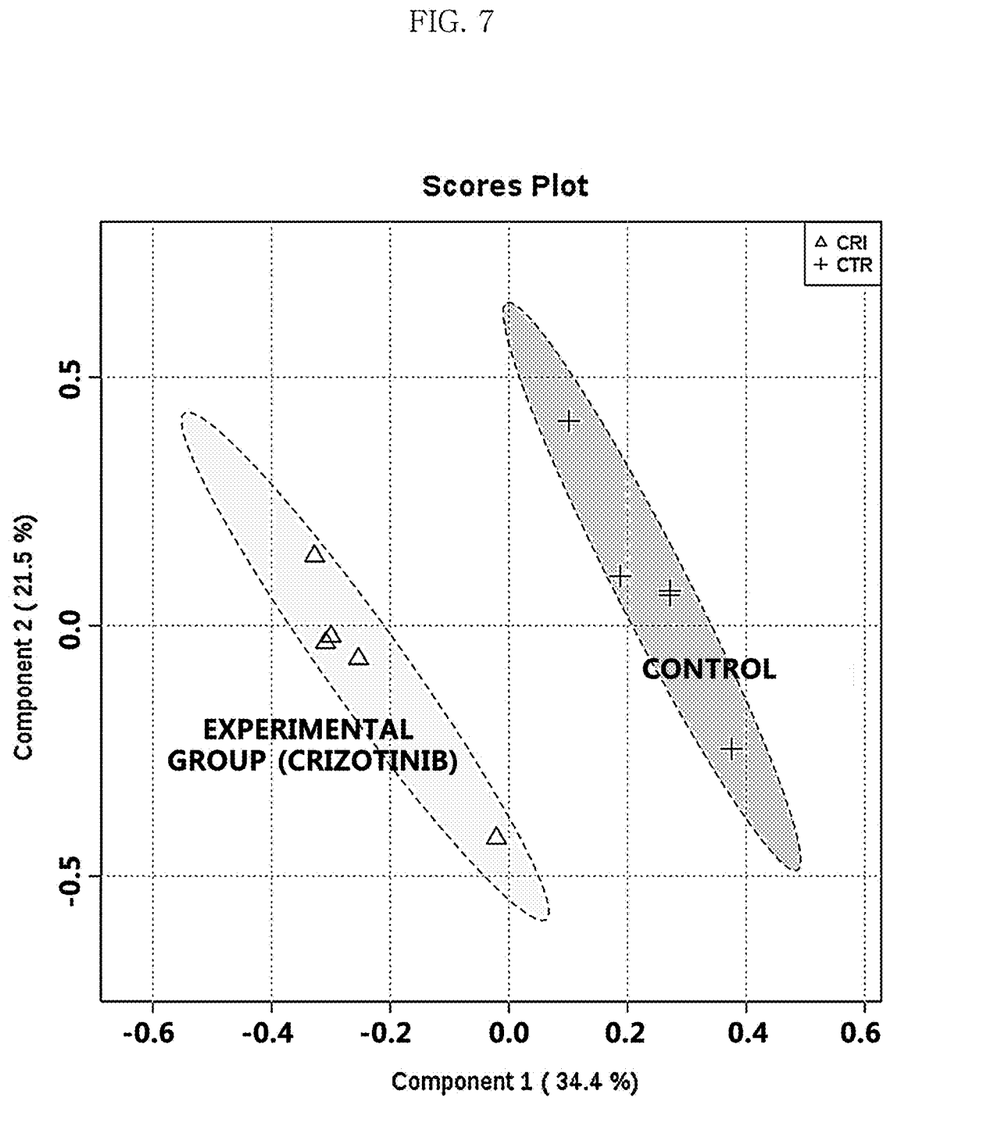
FIG. 7 is a diagram illustrating the results of the chromatogram data analysis of the result values illustrated in FIG. 5.

Partial least squares discriminant analysis (PLS-DA) was conducted in order to analyze the chromatogram data attained in Example 2-3. Specifically, Excel raw data attained by conducting calibration and peak alignment using the compound discovery software of Thermo Fisher Scientific Inc. was extracted from the chromatogram. The total number of extracted raw data was 765. The extracted file was first divided by the internal standard substance and corrected using DNA quantitation of cells, and statistical processing was conducted using SIMCA software. The results are illustrated in FIGS. 6 and 7. The results for the experiment on the HCC-78 cell line are illustrated in FIG. 6, and the results for the experiment on the MCF-7 cell line are illustrated in FIG. 7.

As illustrated in FIGS. 6 and 7, it has been observed that clustering between the control group and each experimental group is clearly distinguished from each other, and it has been confirmed from these results that there is a change in the metabolites in each cell line after drug treatment.

Thereafter, for statistical processing on the experimentally elicited values, the data attained by correcting for the above result values were subjected to a t-test to distinguish the significantly changed data. According to the results of the statistical analysis, substances having a p value of 0.05 or less were classified as metabolites which exhibit a significant change. The classified substances were subjected to qualitative analysis based on databases such as human metabolome database (HMDB), massbank, and metlin based on the m/z value of chromatogram.

As a result, a total of 20 substances were significantly changed in the HCC-78 cell line by the treatment with crizotinib and ceritinib: myristoylcarnitine, 2-furoylglycine, Lyso phosphatidylcholine(16:1(9Z), eicosatetraynoic acid, adenosine, L-prolyl-L-proline, cAMP, hexanoylcarnitine, phosphorylcholine, isobutyryl carnitine, L-glutathione, quinine, 5'-S-methyl-5'-thioadenosine, leucine-leucine, Coenzyme Q2, phosphatidylethanolamine(18:1(9Z)/0:0), LysoPC (18:1(11Z)), AMP, phosphatidylcholine(17:1), phosphatidylcholine(16:0/0:0).

Figure 8:
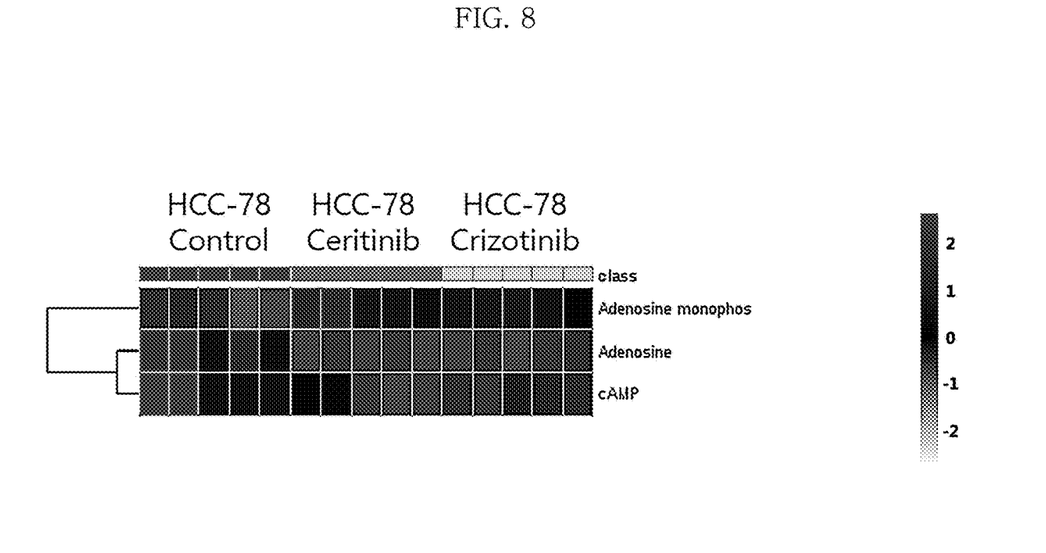
FIG. 8 is a diagram illustrating the results attained by subjecting the data attained by correcting the result values illustrated in FIG. 6 to a t-test as a heat map.
Figure 9:
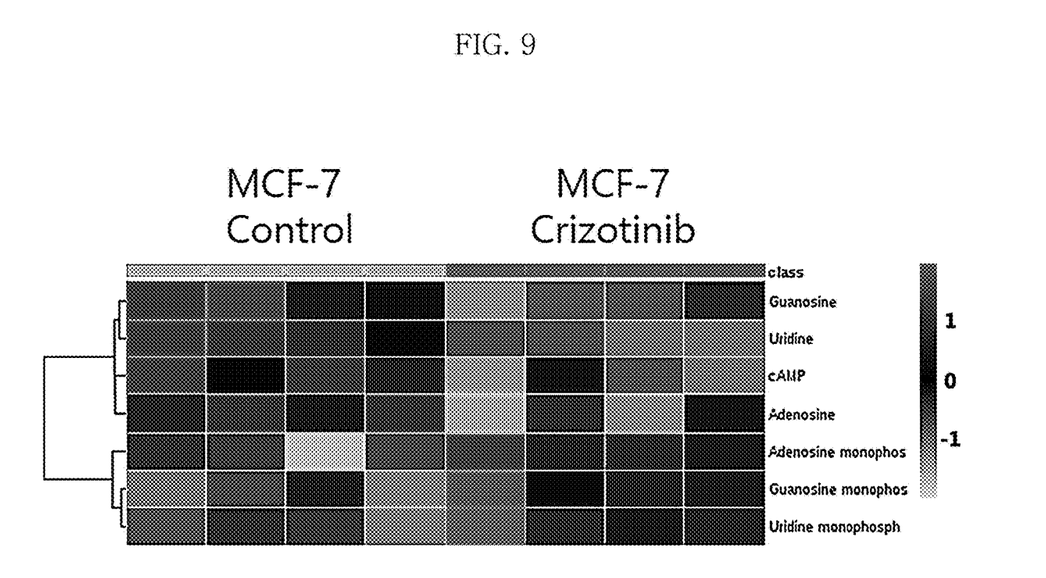
FIG. 9 is a diagram illustrating the results attained by subjecting the data attained by correcting the result values illustrated in FIG. 7 to a t-test as a heat map.
Figure 10:
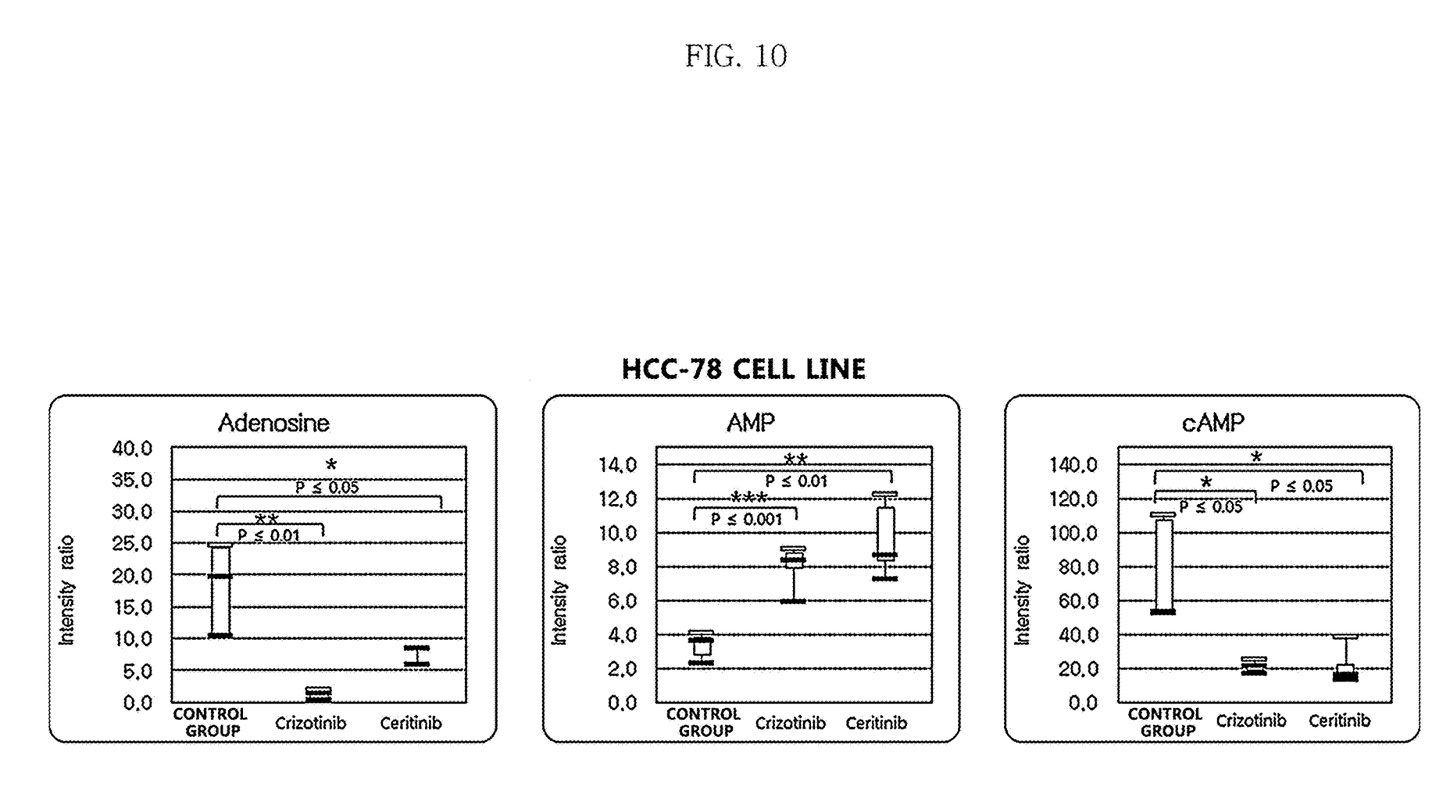
FIG. 10 is a diagram illustrating the results attained by subjecting the data attained by correcting the result values illustrated in FIG. 6 to a t-test as a box-and-whiskers plot.
Figure 11:
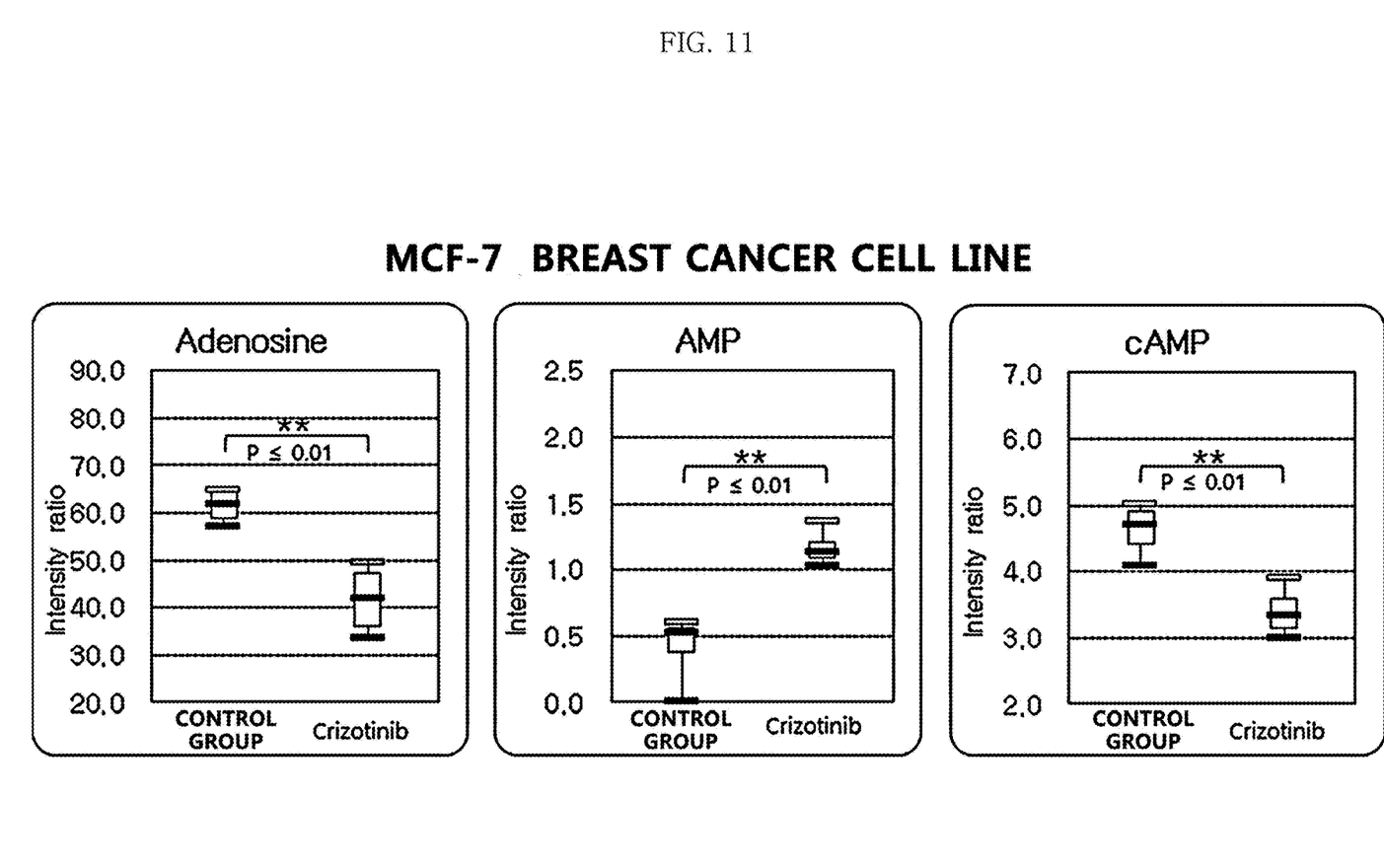
FIG. 11 is a diagram illustrating the results attained by subjecting the data attained by correcting the result values illustrated in FIG. 7 to a t-test as a box-and-whiskers plot.

In the MCF-7 cell line, a total of 28 substances were significantly changed by the treatment with crizotinib: acetylcarnitine, L-carnitine, n-acetyl-DL-aspartic acid, n-acetyl-L-aspartate, L-glutamate, L-tryptophan, malic acid, succinic acid, sebacic acid, palmitoyl-L-carnitine, propionylcarnitine, azelaic acid, 2-arachidonylglycerol/monoachylglyceride, Monoglyceride(0:0/20:4(5Z,8Z,11Z,14Z)/0:0), phosphatidylcholine(34:2), phosphatidylethanolamine (16:0/18:1), AMP, cAMP, adenosine, guanosine, uridine, ketovaline, inosine, uridine monophosphate (UMP), guanidylic acid (guanosine monophosphate), 5'-deoxy-5'-methylthioadenosine, acetylcholine, phosphocholine, taurine. At this time, the change values for some metabolites exhibiting the above change are illustrated in FIGS. 8 and 9 as a heat map and in FIGS. 10 and 11 as a box-and-whiskers plot. Here, FIGS. 8 and 10 illustrate the results for the experiment on the HCC-78 cell line and FIGS. 9 and 11 illustrate the results for the experiment on the MCF-7 cell line.

As can be seen from the above results and FIGS. 8 to 11, AMP, cAMP, and adenosine commonly exhibited a significant change in the HCC-78 and MCF-7 cell lines among the respective metabolites. The metabolites other than these did not exhibit common changes in the HCC-7 and MCF-7 cell lines. At this time, the increase and decrease of the metabolites were more significant in the HCC-78 cell line. Specifically, in the case of the HCC-78 cell line, AMP increased by 140.79%, cAMP decreased by 72.03%, and adenosine decreased by 93.43% as compared with those in the control group when being treated with crizotinib, and AMP increased by 188.21%, cAMP decreased by 66.78%, and adenosine decreased by 95.31% as compared with those in the control group when being treated with ceritinib. In the MCF-7 cell line, AMP increased by 82.91%, cAMP decreased by 28.6%, and adenosine decreased by 32.07% when being treated with crizotinib. These results indicate that AMP, cAMP, and adenosine can be used for screening ALK or ROS-1 kinase inhibitors including crizotinib.

In an aspect, by the method, composition and kit for screening an ALK or ROS-1 kinase inhibitor according to the present disclosure, it is possible to conduct simultaneous quantitative and qualitative analysis and faster screening of a larger number of candidate substances as compared with conventional molecular biological experimental methods and to grasp the overall level of change in a plurality of different metabolites in a cell line by candidate substances of ALK or ROS-1 kinase inhibitor, and thus the screening efficiency for drugs which exert an ALK or ROS-1 kinase inhibitory effect is excellent. Consequently, the present disclosure has an advantage of being able to be used in various ways in the development of new drugs which exert an ALK or ROS-1 kinase inhibitory effect.

While the present disclosure has been described with respect to the specific embodiments, it will be apparent to those skilled in the art that various changes and modifications may be made without departing from the spirit and scope of the disclosure as defined in the following claims.

[Accession Number]
Institution name: Korea Biotechnology Research Institute
Accession number: KCTC13642BP
Accession date: Sep. 17, 2018
Institution name: Korea Biotechnology Research Institute
Accession number: KCTC13643BP
Accession date: Sep. 17, 2018

What is claimed is:

1. A method for screening an anaplastic lymphoma kinase (ALK) or c-ros oncogene 1 (ROS-1) kinase inhibitor, comprising:
   treating a cell line with a candidate substance as said ALK or ROS-1 kinase inhibitor;
   measuring a level of metabolite for each of adenosine, adenosine monophosphate (AMP) and cyclic adenosine monophosphate (cAMP) in the cell line treated with the candidate substance; and
   comparing the measured levels of adenosine, AMP and cAMP with control levels of adenosine, AMP and cAMP, respectively, without candidate substance treatment;
   wherein the measured level of metabolites is analyzed by a multivariate analysis system; and
   wherein:
   the measured level of adenosine in the treated cell line is higher than the control level of adenosine, and the candidate substance is determined as the ALK or ROS-1 kinase inhibitor;
   the measured level of cAMP in the treated cell line is higher than the control level of cAMP, and the candidate substance is determined as the ALK or ROS-1 kinase inhibitor; or
   the measured level of AMP in the treated cell line is lower than the control level of AMP, and the candidate substance is determined as the ALK or ROS-1 kinase inhibitor.

2. The method according to claim 1, wherein the ALK or ROS-1 kinase inhibitor is a drug for cancer treatment.

3. The method according to claim 1, wherein the ALK or ROS-1 kinase inhibitor is one or more of a drug for lung cancer treatment, a drug for breast cancer treatment, a drug for brain cancer treatment, a drug for pancreatic cancer treatment and a drug for colorectal cancer treatment.

4. The method according to claim 1, wherein the cell line is one or more of a lung carcinoma cell line, a breast carcinoma cell line, a brain cancer cell line, a pancreatic cancer cell line and a colorectal cancer cell line.

5. The method according to claim 4, wherein the lung carcinoma cell line is a non-small cell lung carcinoma cell line.

6. The method according to claim 4, wherein the breast carcinoma cell line is a carcinoma in situ of breast cell line.

* * * * *